United States Patent
Ludwin et al.

(10) Patent No.: US 11,033,201 B2
(45) Date of Patent: *Jun. 15, 2021

(54) INCONSISTENT FIELD-BASED PATCH LOCATION COORDINATE CORRECTION

(71) Applicant: BIOSENSE WEBSTER (ISRAEL) LTD., Yokneam (IL)

(72) Inventors: Doron Moshe Ludwin, Haifa (IL); Eitan Peri, Givat Ada (IL); Aharon Turgeman, Zichron Ya'acov (IL); Avigdor Rosenberg, Kiryat Tivon (IL); Menachem Schechter, Kiryat Ata (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 518 days.

This patent is subject to a terminal disclaimer.

(21) Appl. No.: 15/228,627

(22) Filed: Aug. 4, 2016

(65) Prior Publication Data

US 2017/0065205 A1    Mar. 9, 2017

Related U.S. Application Data

(60) Provisional application No. 62/214,273, filed on Sep. 4, 2015.

(51) Int. Cl.
*A61B 5/06* (2006.01)
*A61B 5/283* (2021.01)
(Continued)

(52) U.S. Cl.
CPC .............. *A61B 5/063* (2013.01); *A61B 5/062* (2013.01); *A61B 5/283* (2021.01); *A61B 5/287* (2021.01);
(Continued)

(58) Field of Classification Search
None
See application file for complete search history.

(56) References Cited

U.S. PATENT DOCUMENTS 5,391,199 A    2/1995    Ben-Haim
5,443,489 A    8/1995    Ben-Haim
(Continued)

FOREIGN PATENT DOCUMENTS

EP    2064987 A1    6/2009
EP    2168478 A1    3/2010
(Continued)

OTHER PUBLICATIONS

European Search Report, Application No. 16186940.9-1657, dated Feb. 6, 2017.

(Continued)

*Primary Examiner* — Matthew Kremer
(74) *Attorney, Agent, or Firm* — Notaro, Michalos & Zaccaria P.C.

(57) ABSTRACT

A method uses multiple patches fixed to a surface of a body, the patches including respective electrodes in contact with the surface, and at least one of the patches configured to output a signal in response to a magnetic field applied to the body. Initially, the signal is processed to compute first magnetic and first electrical locations of the at least one of the patches. Subsequently, the signal is processed to compute second magnetic and second electrical locations of the at least one of the patches. A first relation is computed between the first magnetic and electrical locations, and a second relation is computed between the second magnetic and electrical locations. When there is a difference between the first and the second relations, a magnetic location correction is computed responsively to the difference, and (Continued)

the correction is applied in tracking a position of a magnetic tracking sensor inside the body.

18 Claims, 6 Drawing Sheets

(51) Int. Cl.
| | |
|---|---|
| *A61B 5/287* | (2021.01) |
| *A61B 5/361* | (2021.01) |
| *A61B 5/363* | (2021.01) |
| *A61B 5/00* | (2006.01) |
| *A61B 6/12* | (2006.01) |
| *A61B 6/00* | (2006.01) |

(52) U.S. Cl.
CPC .............. *A61B 5/361* (2021.01); *A61B 5/363* (2021.01); *A61B 5/6833* (2013.01); *A61B 6/12* (2013.01); *A61B 6/487* (2013.01); *A61B 5/6852* (2013.01); *A61B 2505/05* (2013.01)

(56) References Cited

U.S. PATENT DOCUMENTS

| | | | |
|---|---|---|---|
| 5,558,091 A | 9/1996 | Acker et al. | |
| 5,899,860 A | 5/1999 | Pfeiffer et al. | |
| 5,944,022 A | 8/1999 | Nardella et al. | |
| 5,983,126 A | 11/1999 | Wittkampf | |
| 6,172,499 B1 | 1/2001 | Ashe | |
| 6,177,792 B1 | 1/2001 | Govari et al. | |
| 6,456,864 B1 | 9/2002 | Swanson et al. | |
| 6,574,498 B1 | 6/2003 | Gilboa | |
| 6,690,963 B2 | 2/2004 | Ben-Haim et al. | |
| 6,788,967 B2 | 9/2004 | Ben-Haim et al. | |
| 8,456,182 B2 | 6/2013 | Bar-Tal et al. | |
| 2005/0143648 A1* | 6/2005 | Minai | A61B 1/041 600/410 |
| 2005/0256398 A1 | 11/2005 | Hastings et al. | |
| 2007/0016007 A1 | 1/2007 | Govari et al. | |
| 2007/0060833 A1 | 3/2007 | Hauck | |
| 2009/0093806 A1 | 4/2009 | Govari et al. | |
| 2009/0137883 A1* | 5/2009 | Chiba | A61B 1/041 600/302 |
| 2009/0138007 A1 | 5/2009 | Govari et al. | |
| 2010/0079158 A1 | 4/2010 | Bar-Tal et al. | |
| 2011/0201969 A1 | 8/2011 | Hatlestad et al. | |
| 2012/0172702 A1* | 7/2012 | Koyrakh | A61B 5/063 600/408 |
| 2012/0172712 A1 | 7/2012 | Bar-Tal | |
| 2012/0265054 A1 | 10/2012 | Olson | |
| 2013/0066193 A1 | 3/2013 | Olson | |
| 2013/0147480 A1 | 6/2013 | Sueoka et al. | |
| 2016/0367168 A1* | 12/2016 | Malinin | A61B 5/068 |
| 2016/0367323 A1* | 12/2016 | Malinin | A61B 5/068 |

FOREIGN PATENT DOCUMENTS

| | | |
|---|---|---|
| EP | 2886054 A1 | 6/2015 |
| WO | WO 2012/092016 A1 | 7/2012 |
| WO | 20140028114 A1 | 2/2014 |
| WO | 2014182822 A1 | 11/2014 |

OTHER PUBLICATIONS

European Search Report for corresponding patent application No. 20183929.7, dated Feb. 24, 2021.

* cited by examiner

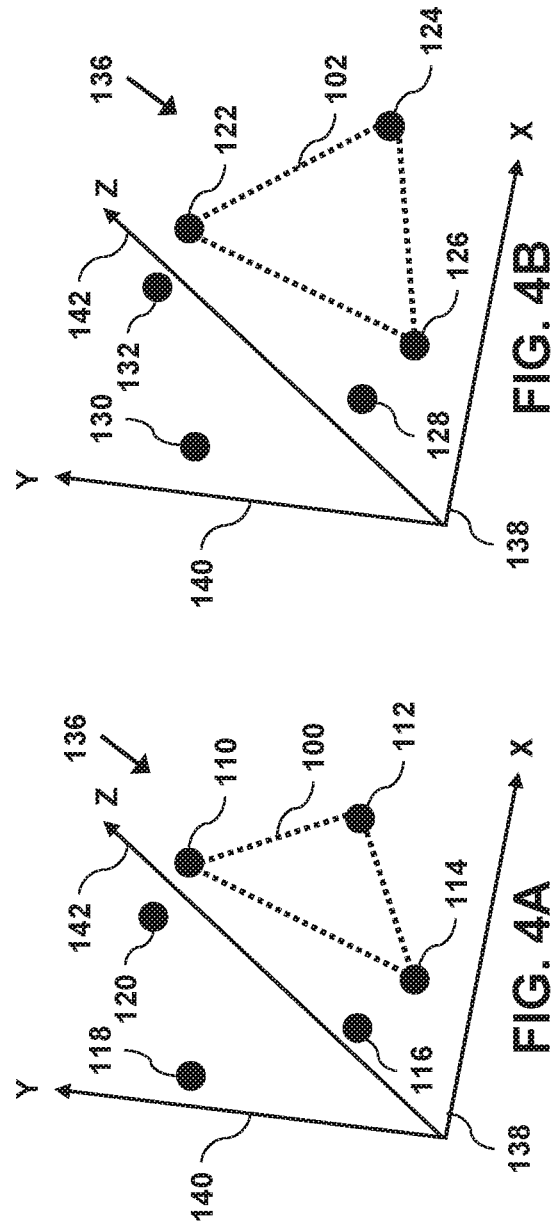
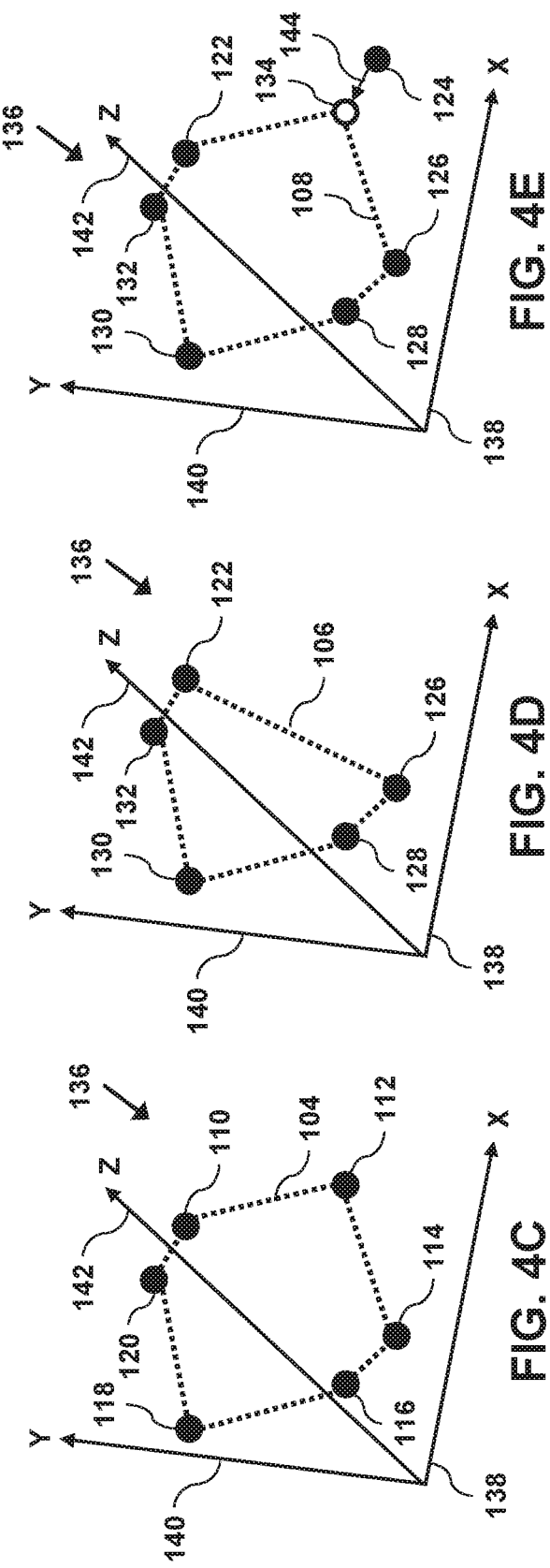

INCONSISTENT FIELD-BASED PATCH LOCATION COORDINATE CORRECTION

CROSS-REFERENCE TO RELATED APPLICATION

This application claims the benefit of U.S. Provisional Patent Application 62/214,273, filed Sep. 4, 2015, which is incorporated herein by reference.

FIELD OF THE INVENTION

The present invention relates generally to medical imaging, and specifically to a method for correcting measurements indicating an inconsistent field-based location coordinates of a skin patch affixed to a patient.

BACKGROUND OF THE INVENTION

A wide range of medical procedures involve placing objects, such as sensors, tubes, catheters, dispensing devices, and implants, within the body. Real-time imaging methods are often used to assist doctors in visualizing the object and its surroundings during these procedures. In most situations, however, real-time three-dimensional imaging is not possible or desirable. Instead, systems for obtaining real-time spatial coordinates of the internal object are often utilized.

U.S. Patent Application 2007/0016007, to Govari et al., whose disclosure is incorporated herein by reference, describes a hybrid magnetic-based and impedance-based position sensing system. The system includes a probe adapted to be introduced into a body cavity of a subject.

U.S. Pat. No. 6,574,498, to Gilboa, whose disclosure is incorporated herein by reference, describes a system for determining the position of a work piece within a cavity of an opaque body. The system claims to use a transducer that interacts with a primary field, and several transducers that interact with a secondary field.

U.S. Pat. No. 5,899,860, to Pfeiffer, et al., whose disclosure is incorporated herein by reference, describes a system for determining the position of a catheter inside the body of a patient. A correction function is determined from the difference between calibration positions derived from received location signals and known, true calibration positions, whereupon catheter positions, derived from received position signals, are corrected in subsequent measurement stages according to the correction function.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The description above is presented as a general overview of related art in this field and should not be construed as an admission that any of the information it contains constitutes prior art against the present patent application.

SUMMARY OF THE INVENTION

There is provided, in accordance with an embodiment of the present invention a method for sensing, using an array of patches fixed to a surface of a body of a subject, the patches including respective electrodes in contact with the surface, and at least one of the patches including a patch sensor configured to output a signal in response to a magnetic field applied to the body, the method including at a first time, processing the signal so as to compute first field-based location coordinates of the at least one of the patches, and computing first impedance-based location coordinates of the at least one of the patches by measuring an impedance to an electrical current applied to the body, at a second time, subsequent to the first time, processing the signal so as to compute second field-based location coordinates of the at least one of the patches, and computing second impedance-based location coordinates of the at least one of the patches by measuring the an impedance to the electrical current, computing a first relation between the first field-based location coordinates and the first impedance-based location coordinates, and a second relation between the second field-based location coordinates and the second impedance-based location coordinates, when there is a difference between the second relation and the first relation, computing a field-based location coordinate correction responsively to the difference, and applying the field-based location coordinate correction in tracking a position of a magnetic tracking sensor inside the body, based on signals received from the magnetic tracking sensor in response to the applied magnetic field.

In embodiments of the present invention, the first relation for a given patch may include a first distance and a first orientation from the first impedance-based location coordinates of the given patch to the first field-based location coordinates of the given patch, and wherein the second relation for the given patch includes a second distance and a second orientation from the second impedance-based location coordinates of the given patch to the second field-based location coordinates of the given patch.

In some embodiments, the field-based location coordinate correction for the second field-based location coordinates of the given patch includes the first distance and the first orientation. In additional embodiments, the method may include at a third time, subsequent to the second time, processing the signal so as to compute third field-based location coordinates of the at least one of the patches, computing third impedance-based location coordinates of the at least one of the patches by measuring the an impedance to the electrical current, and applying the field-based location coordinate correction to the third field-based location coordinates.

In further embodiments, the magnetic field is applied to the body by positioning the body over multiple coils configured to generate the magnetic field. In supplemental embodiments, the object includes a medical probe having a probe electrode, and wherein the electrical current is applied to the body by conveying the electrical current to the probe electrode. In additional embodiments, the signal includes a first signal, and wherein measuring the impedance includes receiving, from the at least one patches, a second signal in response to the impedance of the electrical current conveyed by the probe electrode.

There is also provided, in accordance with an embodiment of the present invention an apparatus for method for sensing, including an array of patches fixed to a surface of a body of a subject, the patches including respective electrodes in contact with the surface, and at least one of the patches including a patch sensor configured to output a signal in response to a magnetic field applied to the body, and a control console configured at a first time, to process the signal so as to compute first field-based location coordinates of the at least one of the patches, and to compute first impedance-based location coordinates of the at least one of the patches by measuring an impedance to an electrical current applied to the body, at a second time, subsequent to the first time, to process the signal so as to compute second field-based location coordinates of the at least one of the patches, and to compute second impedance-based location coordinates of the at least one of the patches by measuring the an impedance to the electrical current, to compute a first relation between the first field-based location coordinates and the first impedance-based location coordinates, and a second relation between the second field-based location coordinates and the second impedance-based location coordinates, when there is a difference between the second relation and the first relation, to compute a field-based location coordinate correction responsively to the difference, and to apply the field-based location coordinate correction in tracking a position of a magnetic tracking sensor inside the body, based on signals received from the magnetic tracking sensor in response to the applied magnetic field.

There is further provided, in accordance with an embodiment of the present invention, a computer software product for sensing, using an array of patches fixed to a surface of a body of a subject, the patches including respective electrodes in contact with the surface, and at least one of the patches including a patch sensor configured to output a signal in response to a magnetic field applied to the body, the product including a non-transitory computer-readable medium, in which program instructions are stored, which instructions, when read by a computer, cause the computer to process, at a first time, the signal so as to compute first field-based location coordinates of the at least one of the patches, and to compute first impedance-based location coordinates of the at least one of the patches by measuring an impedance to an electrical current applied to the body, to process at a second time, subsequent to the first time, the signal so as to compute second field-based location coordinates of the at least one of the patches, and to compute second impedance-based location coordinates of the at least one of the patches by measuring the an impedance to the electrical current, to compute a first relation between the first field-based location coordinates and the first impedance-based location coordinates, and a second relation between the second field-based location coordinates and the second impedance-based location coordinates, when there is a difference between the second relation and the first relation, to compute a field-based location coordinate correction responsively to the difference, and to apply the field-based location coordinate correction in tracking a position of a magnetic tracking sensor inside the body, based on signals received from the magnetic tracking sensor in response to the applied magnetic field.

BRIEF DESCRIPTION OF THE DRAWINGS

The disclosure is herein described, by way of example only, with reference to the accompanying drawings, wherein:

FIGS. 4A-4E are schematic diagrams illustrating rigid bodies that are constructed from locations of the adhesive skin patches in order to correct the inconsistent physical location of the given skin patch, in accordance with an embodiment of the present invention;

DETAILED DESCRIPTION OF EMBODIMENTS

Overview

Various diagnostic and therapeutic procedures involve mapping of the electrical potential on the inner surface of a cardiac chamber. Electrical mapping can be performed, for example, by inserting a medical probe (e.g., a catheter), whose distal end is fitted with a position sensor and a mapping electrode, into the cardiac chamber. The cardiac chamber is mapped by positioning the probe at multiple points on the inner chamber surface. At each point, the electrical potential is measured using the electrode, and the distal end position is measured using the position sensor. The measurements are typically presented as a map of the electrical potential distribution over the cardiac chamber surface.

While positioning the medical probe within the cardiac chamber, impedance-based and/or magnetic-based position sensing systems can be used to determine a location of the probe within the cardiac chamber. Location sensing systems, such as those described in U.S. Pat. No. 8,456,182, whose disclosure is incorporated herein by reference, can determine a location of the probe by using locations of a set of three adhesive skin patches (also referred to herein as patches) that are affixed to a back of a patient. Location measurements received from the patches can be used to define a rigid body in a body coordinate system, and to determine a location of the probe within the rigid body. The body coordinate system can be updated as the adhesive skin patches move due to normal patient activities such as breathing.

Typically, the adhesive skin patches move and have respective locations that are consistent with one another so that the rigid body referred to above does not deform, but there may be instances when movement of one or more of the patches results in each of the one or more patches having a location that is not consistent with locations of the remaining patches. Embodiments of the present invention provide methods and systems for detecting and correcting an inconsistent location of one or more of the adhesive skin patches.

In a disclosed embodiment, the inconsistent location comprises a physical location of one of the adhesive skin patches. For example, if the patient is lying on a table, the one adhesive skin patch may "stick" to the table as the patient moves. In an alternative embodiment, the inconsistent location comprises apparent locations of a plurality of the patches. For example, the positioning system may be based on magnetic sensors, and magnetic interference may cause an "apparent" movement (i.e., not a physical movement) of the plurality of the patches to their respective apparent inconsistent locations.

System Description

Figure 1:
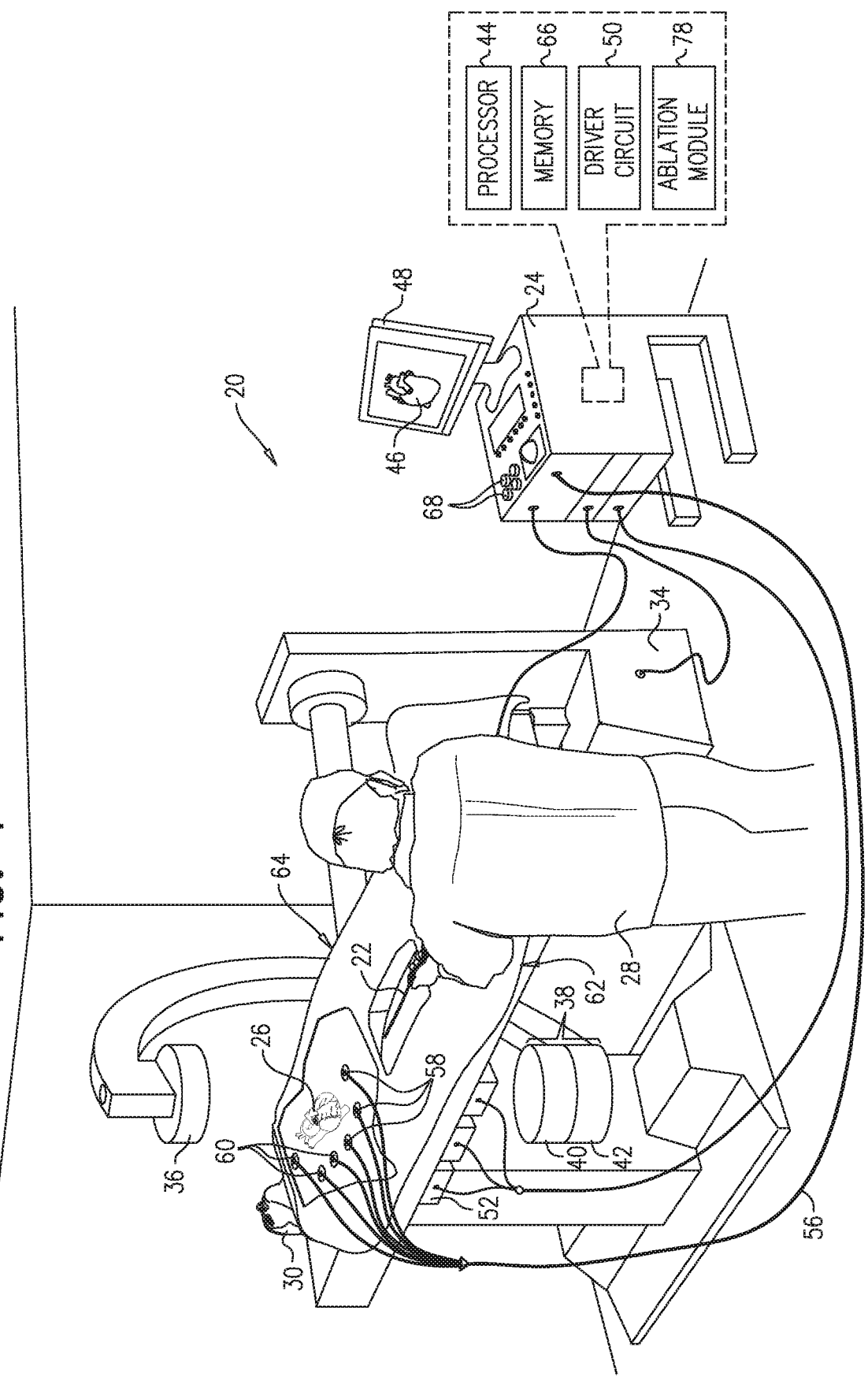
FIG. 1 is a schematic pictorial illustration of a medical system configured to correct an inconsistent location of one or more adhesive skin patches while performing a procedure on a heart, in accordance with an embodiment of the present invention.
Figure 2:
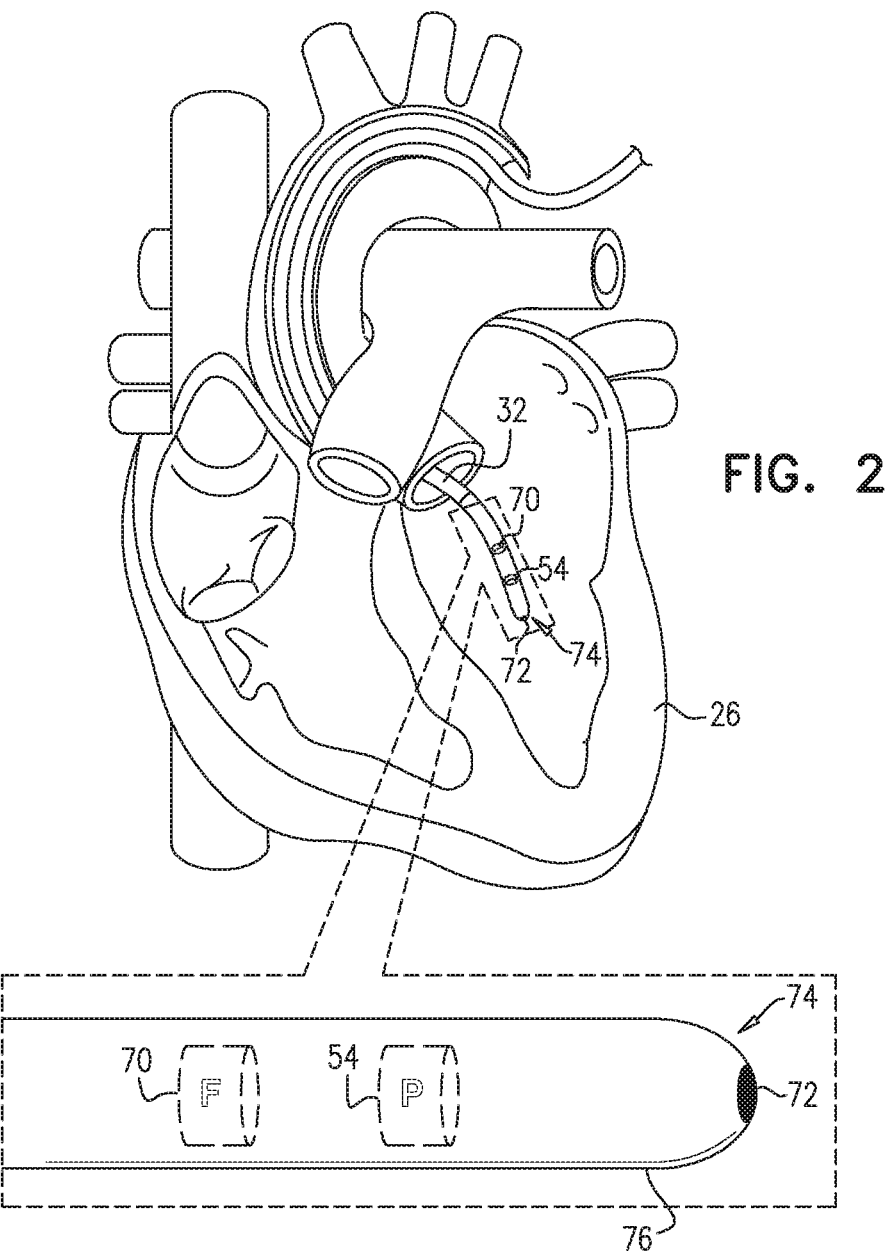
FIG. 2 is a schematic pictorial of a catheter in the heart, in accordance with an embodiment of the present invention.

FIG. 1 is a schematic pictorial illustration of a medical system 20, and FIG. 2 is a schematic illustration of a probe used in the system, in accordance with an embodiment of the present invention. System 20 may be based, for example, on the CARTO® system, produced by Biosense Webster Inc. (Diamond Bar, Calif.). System 20 comprises a medical probe 22, such as a catheter, and a control console 24. In embodiments described hereinbelow, it is assumed that probe 22 is used for diagnostic or therapeutic treatment, such as performing ablation of heart tissue in a heart 26. Alternatively, probe 22 may be used, mutatis mutandis, for other therapeutic and/or diagnostic purposes in the heart or in other body organs.

An operator 28 inserts probe 22 through the vascular system of a patient 30 so that distal end 32 (FIG. 2) of probe 22 enters a chamber of heart 26. In the configuration shown in FIG. 1, operator 28 uses a fluoroscopy unit 34 to visualize distal end 32 inside heart 26. Fluoroscopy unit 34 comprises an X-ray source 36, positioned above patient 30, which transmits X-rays through the patient. A flat panel detector 38, positioned below patient 30, comprises a scintillator layer 40 which converts the X-rays which pass through patient 30 into light, and a sensor layer 42 which converts the light into electrical signals. Sensor layer 42 typically comprises a two dimensional array of photodiodes, where each photodiode generates an electrical signal in proportion to the light detected by the photodiode.

Control console 24 comprises a processor 44 that converts the electrical signals from fluoroscopy unit 34 into an image 46, which the processor presents as information regarding the procedure on a display 48. Display 48 is assumed, by way of example, to comprise a cathode ray tube (CRT) display or a flat panel display such as a liquid crystal display (LCD), light emitting diode (LED) display or a plasma display. However other display devices can also be employed to implement embodiments of the present invention. In some embodiments, display 48 may comprise a touchscreen configured to accept inputs from operator 28, in addition to presenting image 46.

System 20 can use magnetic position sensing to determine position coordinates of distal end 32 inside heart 26. In configurations where system 20 uses magnetic based position sensing, console 24 comprises a driver circuit 50 which drives field generators 52 to generate magnetic fields within the body of patient 30. Typically, field generators 52 comprise coils, which are placed below the patient at known positions external to patient 30. These coils generate magnetic fields in a predefined working volume that contains heart 26. A magnetic field sensor 54 (also referred to herein as position sensor 54) within distal end 32 of probe 22 generates electrical signals in response to the magnetic fields from the coils, thereby enabling processor 44 to determine the position of distal end 32 within the cardiac chamber. Magnetic position tracking techniques are described, for example, in U.S. Pat. Nos. 5,391,199, 6,690,963, 5,443,489, 6,788,967, 5,558,091, 6,172,499 and 6,177,792, whose disclosures are incorporated herein by reference.

Additionally, system 20 can use impedance-based position sensing to determine position coordinates of distal end 32 inside heart 26. In configurations where system 20 uses impedance-based position sensing, position sensor 54 is configured as a probe electrode, typically formed on an insulating exterior surface 76 of the distal end, and console 24 is connected by a cable 56 to body surface electrodes, which comprise three primary adhesive skin patches 58 and one or more ancillary adhesive skin patches 60. In some embodiments, primary adhesive skin patches 58 are affixed to a back 62 of patient 30, and the one or more ancillary adhesive skin patches are affixed to a front 64 of the patient. In operation, processor 44 can determine position coordinates of probe 22 inside heart 26 based on the impedance measured between the probe electrode and patches 58 and 60. Impedance-based position tracking techniques are described, for example, in U.S. Pat. Nos. 5,983,126, 6,456, 864 and 5,944,022, whose disclosures are incorporated herein by reference.

In some embodiments, each patch 58 and 60 may also comprise magnetic field sensors (e.g., coils) that can measure the magnetic fields produced by field generators 52, and convey the magnetic field measurements to console 24. Based on the measurements received from patches 58 and 60, processor 44 can determine current positions for each of the primary and the ancillary adhesive skin patches. Both magnetic-based and impedance-based systems described hereinabove generate signals which vary according to the position of distal end 32.

Processor 44 receives and processes the signals generated by position sensor 54 in order to determine position coordinates of distal end 32, typically including both location and orientation coordinates. The method of position sensing described hereinabove is implemented in the above-mentioned CARTO™ system and is described in detail in the patents and patent applications cited above.

Processor 44 typically comprises a general-purpose computer, with suitable front end and interface circuits for receiving signals from probe 22 and controlling the other components of console 24. Processor 44 may be programmed in software to carry out the functions that are described herein. The software may be downloaded to console 24 in electronic form, over a network, for example, or it may be provided on non-transitory tangible media, such as optical, magnetic or electronic memory media. Alternatively, some or all of the functions of processor 44 may be carried out by dedicated or programmable digital hardware components.

Based on the signals received from probe 22 and other components of system 20, processor 44 drives display 48 to update image 46 to present a current position of distal end 32 in the patient's body, as well as status information and guidance regarding the procedure that is in progress. Processor stores data representing image 46 in a memory 66. In some embodiments, operator 28 can manipulate image 46 using one or more input devices 68. In embodiments, where display 48 comprises a touchscreen display, operator 28 can manipulate image 46 via the touchscreen display.

In the configuration shown in FIG. 2, probe 22 also comprises a force sensor 70 contained within distal end 32 and an ablation electrode 72 mounted on a distal tip 74 of probe 22. Force sensor 70 measures a force applied by distal tip 74 on the endocardial tissue of heart 26 by generating a signal to the console that is indicative of the force exerted by the distal tip on the endocardial tissue. In one embodiment, the force sensor may comprise a magnetic field transmitter and receiver connected by a spring in distal tip 74, and may generate an indication of the force based on measuring the deflection of the spring. Further details of this sort of probe and force sensor are described in U.S. Patent Application Publications 2009/0093806 and 2009/0138007, whose disclosures are incorporated herein by reference. Alternatively, distal end 32 may comprise another type of force sensor.

Electrode 72 typically comprises one or more thin metal layers formed over exterior surface 76 of distal end 32. Console 24 also comprises a radio frequency (RF) ablation module 78. Processor 44 uses ablation module 78 to monitor and control ablation parameters such as the level of ablation power applied via electrode 72. Ablation module 78 may also monitor and control the duration of the ablation that is provided.

Single Patch Location Correction

Figure 3:
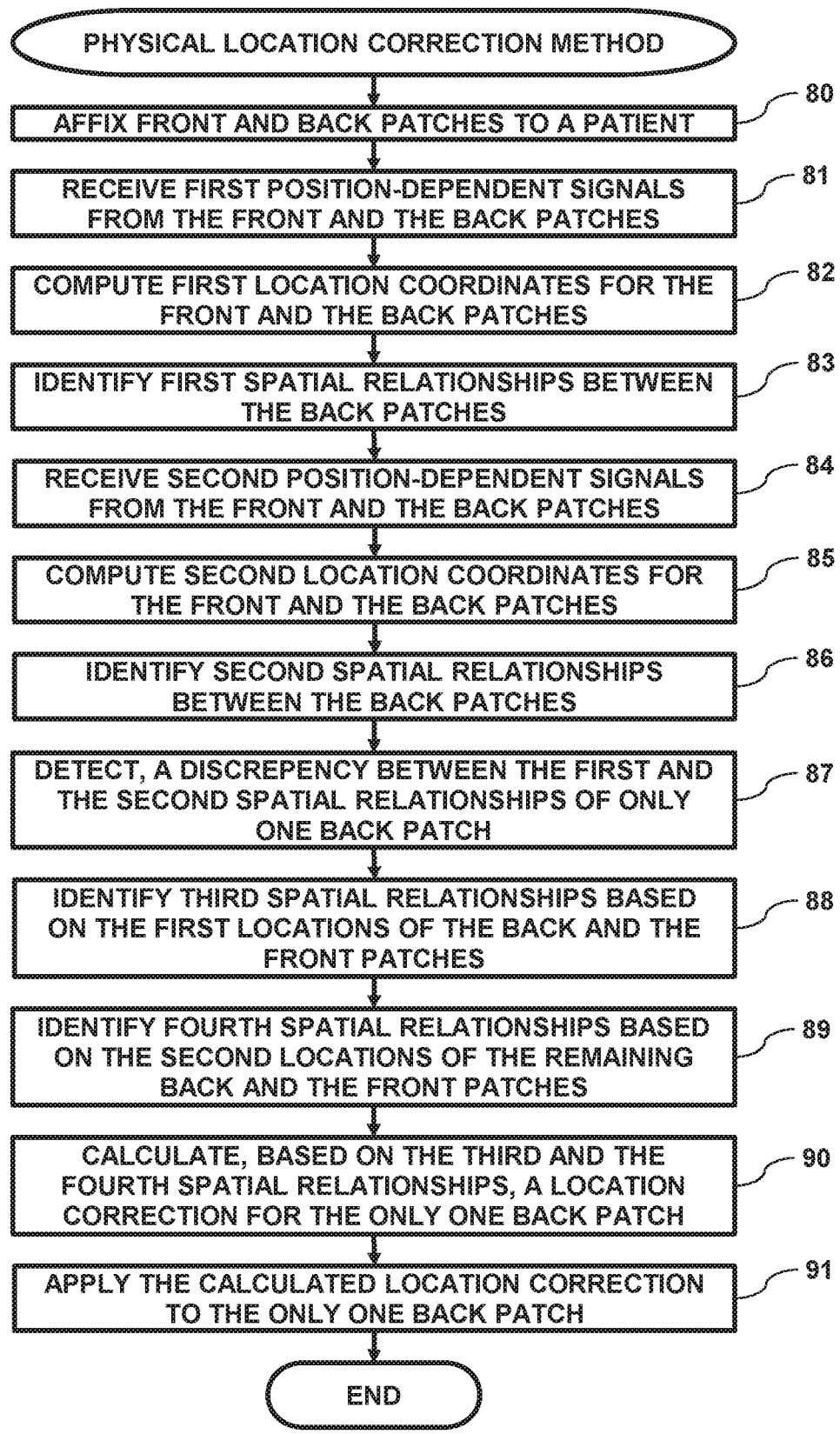
FIG. 3 is a flow diagram that illustrates a method of correcting an inconsistent physical location of a given adhesive skin patch by using location measurements from additional skin patches, in accordance with an embodiment of the present invention.

FIG. 3 is a flow diagram that illustrates a method of correcting an inconsistent physical location of a single primary adhesive skin patch 58 by using location measurements from ancillary patches 60, and FIGS. 4A-4E, referred to collectively as FIG. 4, are schematic diagrams illustrating rigid bodies 100-108 that are constructed from locations 110-134 of the primary and the ancillary skin patches, in accordance with an embodiment of the present invention. In the example shown in FIG. 4, locations 110-132 comprise three-dimensional coordinates in a coordinate system 136 comprising an X-axis 138, a Y-axis 140, and a Z-axis 142.

In embodiments described hereinbelow, locations 110-132 are indicative of spatial relationships that correspond to rigid bodies 100-106. Thus, in the example shown in FIG. 4, locations 110, 112, 114 are indicative of first spatial relationships which define rigid body 100, locations 122, 124, 126 are indicative of second spatial relationships which define rigid body 102, locations 110, 112, 114, 116, 118, 120 are indicative of third spatial relationships which define rigid body 104, and locations 122, 126, 128, 130 and 132 are indicative of fourth spatial relationships which define rigid body 106. In embodiments described herein, rigid body 100 may also be referred to as a first rigid body, rigid body 102 may also be referred to as a second rigid body, rigid body 104 may also be referred to as a third rigid body, and rigid body 106 may also be referred to as a fourth rigid body.

In an initial step 80, operator 28 affixes primary adhesive skin patches 58 to back 62 of patient 30, and affixes ancillary skin patches 60 to front 64 of the patient. In a first receive step 81, processor 44 receives, at a first time, first position-dependent signals from patches 58 and 60. In the flow diagram shown in FIG. 3, primary patches 58 may be referred to as back patches, and ancillary patches 60 may be referred to as front patches.

In a first compute step 82, processor 44 computes respective first location coordinates 110, 112, 114 for patches 58, and respective first location coordinates 116, 118, 120 for patches 60. In a first identification step 83, processor 44 identifies the first spatial relationships between patches 58, using, as shown in FIG. 4A, the respective first location coordinates of locations 110, 112 and 114 of the primary adhesive skin patches, i.e., as rigid body 100.

In a second receive step 84, processor 44 receives, at a second time subsequent to the first time, second position-dependent signals from patches 58 and 60. In a second compute step 85, processor 44 computes respective second location coordinates 122, 124, 126 for patches 58 and respective second location coordinates 128, 130, 132 for patches 60. In a second identification step 86, processor 44 identifies the second spatial relationships between patches 58, using, as shown in FIG. 4B, the respective second location coordinates of locations 122, 124 and 126 of primary adhesive skin patches 58, i.e., as rigid body 102.

In a detection step 87, processor 44 detects a discrepancy between the first and the second spatial relationships. The discrepancy is caused by a change of location of only one primary patch 58 relative to the other primary patches. The detected discrepancy indicates that the second location of the only one primary patch is inconsistent with the second locations of the remaining primary patches 58.

In the present example, the inconsistent location is a result of a physical movement of the only one primary patch 58 from location 112 (FIG. 4A) to location 124 (FIG. 4B) not being consistent with movements of the remaining primary patches from locations 110 and 114 to locations 122 and 126 (i.e., both locations 112 and 124 comprise physical locations of the only one primary patch). For example, processor 44 may detect the discrepancy between the first and the second spatial relationships by detecting that rigid body 100 and rigid body 102 are no longer congruent, and that the non-congruency is effectively caused by the movement of only one of the patch locations defining the bodies. In other words, by detecting the incongruence between rigid bodies 100 and 102, processor 44 detects a discrepancy between the first and the second spatial relationships caused by a given patch 58 that has first location 112 and the other patches 58 that have respective first locations 110 and 114.

In a third identification step 88, processor 44 identifies the third spatial relationships between patches 58 and 60, using, as shown in FIG. 4C, the respective first location coordinates indicated by locations 110, 112, 114, 116, 118, and 120 of the primary and the ancillary skin patches, i.e., as rigid body 104.

During a medical procedure, processor 44 receives signals from all of the primary and the ancillary adhesive skin patches. Typically, as shown in FIGS. 4A and 4B, the processor defines rigid bodies 100 and 102 based on respective locations of primary patches 58. In embodiments of the present invention, upon detecting an inconsistent movement/ location of a given patch 58, processor 44 can calculate a correction for location 124 of the given patch by using locations of ancillary patches 60 and the remaining primary patches to create rigid bodies 104 (FIG. 4C), 106 (FIG. 4D) and 108 (FIG. 4E), as explained hereinbelow.

In a fourth identification step 89, processor 44 identifies the fourth spatial relationships between patches 60 and the other patches 58 (i.e., the fourth spatial relationships do not include the given patch 58 that moved inconsistently), using, as shown in FIG. 4D, the respective second location coordinates of locations 122, 126, 128, 130 and 132 of the primary and the ancillary adhesive skin patches, i.e., as rigid body 106.

In a calculation step 90, processor 44 calculates, based on the spatial relationships, a location correction for the only one primary patch. In some embodiments, the spatial relationships comprise the third and the fourth spatial relationships. Finally, in an application step 91, processor 44 applies the location correction to the second location of the only one primary patch, thereby determining a corrected second location for the only one primary patch, and the method ends. In some embodiments, processor 44 applies the location correction while using the second location coordinates of patches 58 in order to track an object such as probe 22 in the patient's body.

To calculate the location correction using the third and the fourth spatial relationships (i.e., rigid bodies 104 and 106), processor 44 can determine corrected second location 134 for the only one primary patch by determining, based on rigid body 104, an expected second location (i.e., the corrected second location) for the only one primary patch in rigid body 106 (as indicated by an arrow 144), thereby defining rigid body 108. Location 134 comprises a three-dimensional coordinates in coordinate system 136.

Once processor 44 has calculated the location correction for the only one primary patch, processor 44 can apply the location correction to subsequent signals indicating subsequent locations of the only one primary patch. Therefore, upon processor 44 receiving, at a third time subsequent to the second time, third position-dependent signals from the only one primary patch, the processor can compute, based on the third position-dependent signals, third location coordinates for the only one primary patch, and apply the location correction to the third location of the only one primary patch, thereby determining a corrected third location for the only one primary patch.

While embodiments described herein use three ancillary patches 60 to correct an inconsistent movement of only one primary patch 58, configurations comprising any number of ancillary patches 60 whose respective location measurements can be used to define rigid bodies 104, 106 and 108 are considered to be within the spirit and scope of the present invention. Therefore, in embodiments of the present invention, at least four adhesive patches (i.e., three primary patches 58 and at least one ancillary patch 60) may be affixed to patient 30.

Multiple Patch Location Correction

Figure 5:
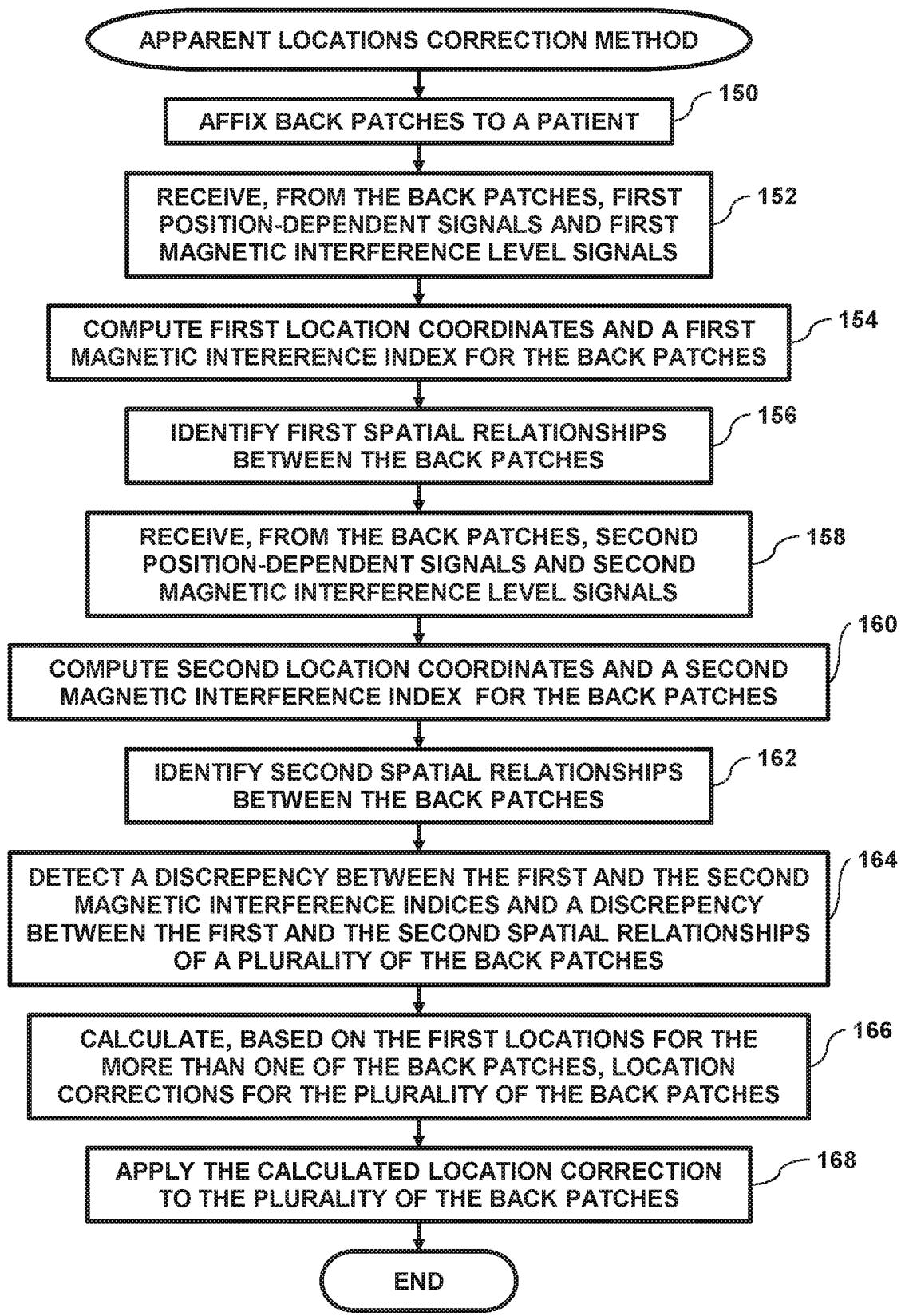
FIG. 5 is a flow diagram that illustrates a method of correcting an inconsistent apparent location of multiple adhesive skin patches caused by magnetic interference, in accordance with an embodiment of the present invention.
Figure 6C:
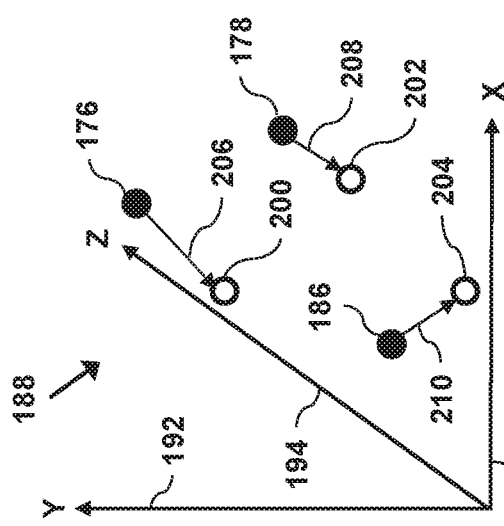
FIGS. 6A-6C are schematic diagrams illustrating first, second and corrected second location coordinates for the multiple adhesive skin patches, in accordance with an embodiment of the present invention.
Figure 6B:
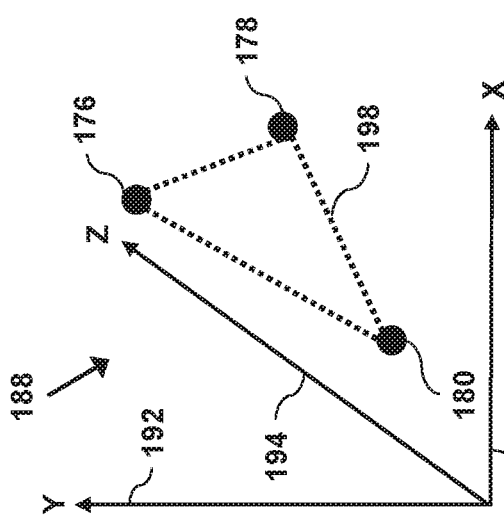
Figure 6A:
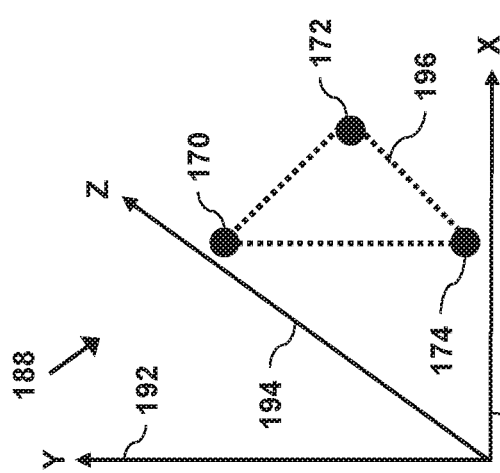

FIG. 5 is a flow diagram that illustrates a method of correcting inconsistent apparent locations of a plurality of primary adhesive skin patch 58, and FIGS. 6A-6C, referred to collectively as FIG. 6, are schematic diagrams illustrating first patch location coordinates 170-174, second patch location coordinates 176-180 and corrected second patch location coordinates 182-186, in accordance with an embodiment of the present invention.

In the example shown in FIG. 6, locations 170-186 comprise three-dimensional coordinates in a coordinate system 188 comprising an X-axis 190, a Y-axis 192, and a Z-axis 194. In embodiments described herein, locations 170-174 are indicative of first spatial relationships represented by a rigid body 196, and locations 176-180 are indicative of second spatial relationships indicated by a rigid body 198.

In an initial step 150, operator 28 affixes primary adhesive skin patches 58 to back 62 of patient 30, and in a first receive step 152, processor 44 receives, at a first time, first position-dependent signals from patches 58. The first position-dependent signals are generated using the magnetic position sensing referred to above. In embodiments of the present invention, the first position-dependent signals may also indicate a first magnetic interference level for each primary patch 58. In the example shown in FIG. 1, the magnetic interference level(s) typically provide a measure of a proximity of X-ray source 36 to field generators 52. In the flow diagram shown in FIG. 5, primary patches 58 may also be referred to as back patches.

In a first compute step 154, processor 44 computes respective first location coordinates and computes a first magnetic interference index (i.e., a value) based on the first magnetic interference levels. In a first identification step 156, processor 44 identifies the first spatial relationships between primary patches 58, using, as shown in FIG. 6A, the respective first location coordinates of locations 170, 172 and 174 of the primary adhesive patches, i.e., as rigid body 196.

In a second receive step 158, processor 44 receives, at a second time subsequent to the first time, second position-dependent signals from primary patches 58. In embodiments of the present invention, the second position-dependent signals may also indicate a second magnetic interference level for each primary patch 58.

In a second compute step 160, processor 44 computes respective second location coordinates and respective second magnetic interference levels for each primary patch 58, and computes a second magnetic interference index based on the second magnetic interference levels. In a second identification step 162, the processor identifies the second spatial relationships between primary patches 58, using, as shown in FIG. 6B, the respective second location coordinates of locations 176, 178 and 180 of the primary adhesive skin patches, i.e., as rigid body 198.

In a detection step 164, processor 44 detects a discrepancy between the first and the second magnetic indices and a discrepancy between the first and the second spatial relationships of a plurality of primary patches 58 relative to the other primary patches. The detected discrepancy indicates that the second locations of a plurality of primary patches 58 are inconsistent with the second locations of the remaining primary patches 58.

In the present example, location 176 comprises a physical first location of a first given primary patch 58, location 178 comprises a physical first location of a second given primary patch 58, location 182 comprises an apparent second location of the first given primary patch, and location 186 comprises an apparent second location of the second given primary patch. In embodiments of the present invention, the inconsistent (i.e., apparent) locations are a result of a difference between the first and the second magnetic field measurements, the difference causing an apparent movement of the first and the second given primary patches from locations 170, 172 and 174 (FIG. 6A) to locations 176, 178 and 180 (FIG. 6B). In some embodiments, processor 44 can detect the discrepancy between the first and the second spatial relationships by detecting a difference between rigid body 196 and rigid body 198.

In a calculation step 166, processor 44 calculates, based on the first location coordinates, location corrections for the plurality of primary patches. In some embodiments, the location correction for a given patch 58 comprises a distance and orientation from the second location of the given patch to the first location of the given patch (or vice versa). Finally, in an application step 168, processor 44 applies the location corrections to the second locations of the plurality of the primary patches, thereby determining corrected second locations for the plurality of the primary patches, and the method ends.

In the example shown in FIG. 6, based on the distances and the orientations are indicated by arrows 206, 208 and 210, processor 44 determines corrected second locations 200, 202 and 204 for the plurality of the primary patches. Locations 200, 202 and 204 comprise three-dimensional coordinates in coordinate system 188. In embodiments where the detected movement of patches 58 is caused by magnetic interference (i.e., the detected movement is apparent), then the corrected location coordinates are in accordance with the first location coordinates. Therefore, in the example shown in FIG. 6, location 200 is in accordance with location 170, location 202 is in accordance with location 202, and location 174 is in accordance with location 204.

Once processor 44 has calculated the location correction for patches 58, processor 44 can apply the location correction to subsequent signals indicating subsequent locations of the back patches. Therefore, upon processor 44 receiving, at a third time subsequent to the second time, third position-dependent signals from patches 58, the processor can compute, based on the third position-dependent signals, third location coordinates for the back patches, and apply the location correction to the third locations of the back patches, thereby determining a corrected third location for patches 58.

In embodiments of the present invention, processor 44 can track an object (e.g., probe 22) in the patient's body relative to the respective location coordinates of patches 58 while applying the respective location corrections to the respective location coordinates of the patches. Additionally, while embodiments described herein use three primary patches 58 whose respective location measurements can be used to define rigid bodies 100-108 and 196-198, configurations comprising more than three patches 58 are considered to be within the spirit and scope of the present invention.

It will be understood that the description above provides two embodiments for locating and correcting inconsistent second locations of one or more patches 58. In a first embodiment, as described supra in the description referencing FIGS. 3 and 4, processor 44 detects an inconsistent second location for only one patch 58, but does not detect a discrepancy in the magnetic interference index between the first and the second times. In a second embodiment, as described supra in the description referencing FIGS. 5 and 6, processor 44 detects respective inconsistent second locations for a plurality of patches 58 while detecting a discrepancy in the in the magnetic interference index between the first and the second times.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method for sensing, using an array of patches for being fixed to a surface of a body of a subject, the patches including respective electrodes in contact with the surface, and at least one of the patches including a patch sensor configured to output a signal in response to a magnetic field applied to the body, the method comprising:
    Applying the magnetic field to the body generated by one or more field generators external to the body;
        at a first time, processing the signal output in response to the magnetic field applied to the body so as to compute first field-based location coordinates of the at least one of the patches, and computing first impedance-based location coordinates of the at least one of the patches by measuring impedance when electrical current is applied to the body;
        at a second time, subsequent to the first time, processing the signal output in response to the magnetic field applied to the body so as to compute second field-based location coordinates of the at least one of the patches, and computing second impedance-based location coordinates of the at least one of the patches by measuring the impedance when the electrical current is applied to the body;
    computing a first relation between the first field-based location coordinates and the first impedance-based location coordinates, and a second relation between the second field-based location coordinates and the second impedance-based location coordinates;
    when there is a difference between the second relation and the first relation, computing a field-based location coordinate correction; and
    applying the field-based location coordinate correction in tracking a position of a magnetic tracking sensor inside the body, based on signals received from the magnetic tracking sensor in response to the applied magnetic field.

2. The method according to claim 1, wherein the first relation for the at least one of the patches comprises a first distance and a first orientation from the first impedance-based location coordinates of the at least one of the patches to the first field-based location coordinates of the at least one of the patches, and wherein the second relation for the at least one of the patches comprises a second distance and a second orientation from the second impedance-based location coordinates of the at least one of the patches to the second field-based location coordinates of the at least one of the patches.

3. The method according to claim 2, wherein the field-based location coordinate correction is computed by applying the respective distance and orientation of the first relation to the second impedance-based location coordinates.

4. The method according to claim 1, and comprising at a third time, subsequent to the second time, processing the signal from the patch sensor so as to compute third field-based location coordinates of the at least one of the patches, computing third impedance-based location coordinates of the at least one of the patches by measuring the impedance when the electrical current is applied to the body, and applying the field-based location coordinate correction to the third field-based location coordinates.

5. The method according to claim 1, wherein the magnetic field is applied to the body by positioning the body over multiple coils configured to generate the magnetic field.

6. The method according to claim 1, wherein the magnetic tracking sensor comprises a medical probe having a probe electrode, and wherein the electrical current is applied to the body by conveying the electrical current to the probe electrode.

7. The method according to claim 6, wherein the signal from the patch sensor comprises a first signal, and wherein measuring the impedance comprises receiving, from the at least one of the patches, a second signal in response the impedance when the electrical current is conveyed by the probe electrode.

8. The method according to claim 1, wherein the field-based location coordinate correction is based on the second impedance-based location coordinates.

9. An apparatus for sensing, comprising:
    an array of patches for being fixed to a surface of a body of a subject, the patches including respective electrodes for being placed in contact with the surface, and at least one of the patches including a patch sensor configured to output a signal in response to a magnetic field applied to the body;
    one or more field generators for generating the magnetic field;
    an electrode for insertion in the body,
    a magnetic tracking sensor for insertion in the body,
    a control console configured:
        at a first time, to process the signal output in response to the magnetic field applied to the body so as to compute first field-based location coordinates of the at least one of the patches, and to compute first impedance-based location coordinates of the at least one of the patches by measuring an impedance when electrical current is applied to the body, at a second time, subsequent to the first time, to process the signal output in response to the magnetic field applied to the body so as to compute second field-based location coordinates of the at least one of the patches, and to compute second impedance-based location coordinates of the at least one of the patches by measuring the impedance when the electrical current is applied to the body, to compute a first relation between the first field-based location coordinates and the first impedance-based location coordinates, and a second relation between the second field-based location coordinates and the second impedance-based location coordinates, when there is a difference between the second relation and the first relation, to compute a field-based location coordinate correction, and to apply the field-based location coordinate correction in tracking a position of the magnetic tracking sensor, based on signals received from the magnetic tracking sensor in response to the applied magnetic field.

10. The apparatus according to claim 9, wherein the first relation for the at least one of the patches comprises a first distance and a first orientation from the first impedance-based location coordinates of the at least one of the patches to the first field-based location coordinates of the at least one of the patches, and wherein the second relation for the at least one of the patches comprises a second distance and a second orientation from the second impedance-based location coordinates of the at least one of the patches to the second field-based location coordinates of the at least one of the patches.

11. The apparatus according to claim 10, wherein the field-based location coordinate correction is computed by applying the respective distance and orientation of the first relation to the second impedance-based location coordinates.

12. The apparatus according to claim 9, wherein the control console is configured at a third time, subsequent to the second time, to process the signal from the patch sensor so as to compute third field-based location coordinates of the at least one of the patches, to compute third impedance-based location coordinates of the at least one of the patches by measuring the impedance between the at least one of the patches and the electrode, and to apply the field-based location coordinate correction to the third field-based location coordinates.

13. The apparatus according to claim 9, wherein the one or more field generators include multiple coils adapted to be located under the body for generating the magnetic field.

14. The apparatus according to claim 9, wherein the magnetic tracking sensor comprises a medical probe having a probe electrode.

15. The apparatus according to claim 14, wherein the signal from the patch sensor comprises a first signal, and wherein the control console is configured to measure the impedance by receiving, from the at least one of the patches, a second signal in response to the impedance when the electrical current is conveyed by the probe electrode.

16. The apparatus according to claim 9, wherein the field-based location coordinate correction is based on the second impedance-based location coordinates.

17. A computer software product for sensing, using an array of patches for being fixed to a surface of a body of a subject, the patches including respective electrodes in contact with the surface, and at least one of the patches including a patch sensor configured to output a signal in response to a magnetic field applied to the body by one or more field generators external to the body, the product comprising a non-transitory computer-readable medium, in which program instructions are stored, which instructions, when read by a computer, cause the computer:

to process, at a first time, the signal output from the patch sensor in response to the magnetic field applied to the body so as to compute first field-based location coordinates of the at least one of the patches, and to compute first impedance-based location coordinates of the at least one of the patches based on impedance measurements from the electrode at the first time when electrical current is applied to the body;

to process at a second time, subsequent to the first time, the signal output from the patch sensor in response to the magnetic field applied to the body so as to compute second field-based location coordinates of the at least one of the patches, and to compute second impedance-based location coordinates of the at least one of the patches based on impedance measurements from the electrode at the second time when the electrical current is applied to the body;

to compute a first relation between the first field-based location coordinates and the first impedance-based location coordinates, and a second relation between the second field-based location coordinates and the second impedance-based location coordinates;

when there is a difference between the second relation and the first relation, to compute a field-based location coordinate correction; and to apply the field-based location coordinate correction in tracking a position of a magnetic tracking sensor inside the body, based on signals received from the magnetic tracking sensor in response to the applied magnetic field; and to monitor and control a level of ablation power and a duration of ablation applied via the electrode.

18. The computer software product of claim 17, wherein the field-based location coordinate correction is based on the second impedance-based location coordinates.

* * * * *